United States Patent [19]

Wallfahrer et al.

[11] Patent Number: 5,176,841

[45] Date of Patent: Jan. 5, 1993

[54] COMPOSITIONS FROM α,β-UNSATURATED DICARBOXYLIC ACID ESTERS AND OLEFINICALLY UNSATURATED COMPOUNDS WHICH ARE PARTICULARLY SUITABLE FOR USE AS LUBRICANTS AND LUBRICANT ADDITIVES AND A PROCESS FOR THE PREPARATION OF SUCH COMPOSITIONS

[75] Inventors: Uwe H. Wallfahrer, Nideggen; Marius C. Verploegh; Heribert J. Macherey, both of Kreuzau, all of Fed. Rep. of Germany

[73] Assignee: Akzo N.V., Arnhem, Netherlands

[21] Appl. No.: 611,240

[22] Filed: Nov. 9, 1990

[30] Foreign Application Priority Data

Nov. 17, 1989 [EP] European Pat. Off. ............ 89202923
Nov. 17, 1989 [EP] European Pat. Off. ............ 89202924

[51] Int. Cl.⁵ ................ C10M 107/28; C10M 145/16
[52] U.S. Cl. ................................ 252/56 D; 525/227; 525/384; 525/328.1
[58] Field of Search ............. 252/56 D; 525/227, 384, 525/328.1

[56] References Cited

U.S. PATENT DOCUMENTS

| | | | |
|---|---|---|---|
| 3,381,022 | 4/1968 | Le Suer | 252/56 D |
| 3,396,111 | 8/1968 | Smith et al. | 252/56 D |
| 3,412,111 | 11/1968 | Irwin et al. | |
| 3,819,660 | 6/1974 | Cahill | |
| 4,192,930 | 3/1980 | Beck et al. | |
| 4,255,340 | 3/1981 | Powell | |
| 4,396,774 | 8/1983 | Schaffhausen | |
| 4,581,464 | 4/1986 | Ross et al. | |
| 4,720,555 | 1/1988 | Nash | |
| 4,761,488 | 8/1988 | Fried | |
| 4,863,624 | 9/1989 | Emert et al. | 252/56 D |

FOREIGN PATENT DOCUMENTS 954901 8/1964 United Kingdom.

*Primary Examiner*—Jacqueline Howard
*Attorney, Agent, or Firm*—Ralph J. Mancini; Louis A. Morris

[57] ABSTRACT

In accordance with the present invention, there is provided a composition comprising the reaction product of particular (1) α,β-unsaturated dicarboxylic acid esters and (2) olefinically unsaturated compounds, wherein the resulting composition comprises a substantial amount of an intermediate molecular weight reaction product which is neither the well-known lower molecular weight alkenyl or alkyl succinic reaction product, nor the well-known polymerization reaction product, of (1) and (2). The compositions of the present invention are particularly suitable for use as lubricants and lubricant additives. In accordance with the present invention, there is also provided a process for the preparation of such compositions suitable for use as a lubricant or lubricant additive wherein components (1) and (2) are reacted in the presence of an effective amount of a polymerization inhibitor and/or in the absence of oxygen.

31 Claims, No Drawings

COMPOSITIONS FROM α,β-UNSATURATED DICARBOXYLIC ACID ESTERS AND OLEFINICALLY UNSATURATED COMPOUNDS WHICH ARE PARTICULARLY SUITABLE FOR USE AS LUBRICANTS AND LUBRICANT ADDITIVES AND A PROCESS FOR THE PREPARATION OF SUCH COMPOSITIONS

BACKGROUND OF THE INVENTION

The present invention relates generally to compositions produced from α,β-unsaturated dicarboxylic compounds and olefinically unsaturated compounds, which compositions possess properties making them particularly suitable for use as lubricants and lubricant additives.

Compositions comprising reaction products of α,β-unsaturated dicarboxylic compounds and olefinically unsaturated compounds are generally known in the art. These reaction products have been described in the literature as having a large number of uses ranging from lubricants to emulsifiers, coating additives to cosmetics, protective colloids to dispersants, and detergents to plasticizers.

One particular type of such reaction products, i.e. intermediates in the production of polycondensation products, is known from GB 1 173 643. This reference discloses a specific, high pressure process which produces unsaturated tetracarboxylic acids by reacting an olefin with a 1,2-unsaturated 1,2-dicarboxylic acid or a functional derivative thereof. Suitable reactants to produce the tetracarboxylic acids are lower alkyl olefins. Preferred are branched olefins, with the olefin exemplified being isobutene.

The prior art further describes several schemes for reacting α,β-unsaturated dicarboxylic and olefin compounds: however, the compositions produced by these known reaction schemes comprise essentially one or both of only two types of reaction products—lower molecular weight ene (alkenyl succinic) products and higher molecular weight polymerization products.

When reacting α,β-unsaturated dicarboxylic compounds with olefins, the difference between producing the lower molecular weight alkenyl succinic product and the higher molecular weight polymerization products is normally due to the presence or absence of a polymerization initiator in the reaction mixture.

For example, U.S. Pat. No. 4,192,930, DE-A-3223694, EP-B-0075216 and JP Laid-Open 80/157687 (all of which are incorporated by reference herein for all purposes) teach the production of the higher molecular weight polymerization products by reacting α,β-unsaturated dicarboxylic compounds and olefins in the presence of polymerization initiators such as peroxy compounds.

On the other hand, U.S. Pat. No. 3,381,022 (incorporated by reference herein for all purposes) teaches the production of alkenyl succinic compounds (and the hydrogenated alkyl succinic corresponding compounds) by reacting the above-mentioned components without the polymerization initiator.

To improve the efficiency of the ene reaction and increase selectivity toward the alkenyl succinic products, U.S. Pat. No. 3,819,660, U.S. Pat. No. 4,255,340, U.S. Pat. No. 4,396,774 and U.S. Pat. No. 4,761,488 (all of which are incorporated by reference herein for all purposes) teach the reaction of α,β-unsaturated dicarboxylic acids and anhydrides with olefins in the presence of particular ene reaction catalysts (accelerators).

To achieve like results in increasing selectivity toward alkenyl succinic anhydrides, U.S. Pat. No. 3,412,111, U.S. Pat. No. 4,581,464 and JP Laid Open 82/32276 (all of which are also incorporated by reference herein for all purposes) teach the addition of a particular polymerization inhibitor to the reaction of α,β-unsaturated dicarboxylic anhydrides and olefins. As indicated in the examples of U.S. Pat. No. 3,412,111, the use of the polymerization inhibitor does indeed appear to significantly improve selectivity toward the alkenyl succinic product.

Long chain hydrocarbyl polysuccinic anhydrides are known from U.S. Pat. No. 4,720,555, in which a method is disclosed which comprises the reaction of a long chain hydrocarbon with an excess of maleic anhydride in the absence of a solvent.

Further it is mentioned that a process for the preparation of substituted carboxylic acids wherein a mono olefin is reacted with an unsaturated, conjugated dicarboxyl compound is known from GB 954 901. The obtained products are useful as rust inhibitors in lubricating oils.

It should be noted that generally α,β-unsaturated dicarboxylic acid esters are recognized to be less reactive with olefins than their acid and anhydride counterparts. This prejudice to the use of esters in an ene selective reaction scheme is also apparent from previously mentioned GB 1 173 643. The unsaturated carboxylic compounds exemplified therein, diethyl esters of maleate and fumarate, do react to form the specific tetracarboxylic acid, but the conversion is poor. Previously mentioned GB 954 901 makes a distinction between various carboxylic compounds and, in line with further prior art, does not actually make use of esters, teaching that carboxylic anhydrides are to be preferred. In view of their low reactivity, esters are further utilized only in the polymerization reactions as described, for example, in previously incorporated DE-A-3223694.

It has now surprisingly been discovered that, using the appropriate esters and olefins, compositions can be prepared as is further described below which comprise a substantial amount of an intermediate molecular weight reaction product which is neither the known lower molecular weight alkenyl succinic nor the known higher molecular weight polymeric reaction product.

SUMMARY OF THE INVENTION

In accordance with the present invention, there is provided a composition suitable for use as a lubricant or lubricant additive, which composition comprises the reaction product of (1) an α,β-unsaturated dicarboxylic compound and (2) an olefinically unsaturated compound, wherein the α,β-unsaturated dicarboxylic compound is comprised of at least one ester selected from the group consisting of fumaric esters and maleic esters, wherein the esterifying component comprises a monoalcohol having from 4 to 20 carbon atoms;

the olefinically unsaturated compound comprises a monoolefinically unsaturated compound having from 12 to 24 carbon atoms; and the composition comprises a substantial amount of an intermediate molecular weight reaction product of (1) and (2) which intermediate molecular weight reaction product is neither the lower molecular weight ene reaction product nor the higher molecular weight polymerization product of (1) and (2).

In order to prepare the compositions in accordance with the present invention generally three routes can be followed, viz. (i) reacting (1) and (2) in the presence of a polymerization inhibitor, (ii) reacting (1) and (2) under the exclusion of oxygen, or (iii) stepwise dosage of the ester (1) to the reaction mixture comprising olefin (2). In order to prepare the compositions in accordance with the present invention said routes may be combined in any possible manner, e.g. stepwise dosage of the ester (1) to the reaction mixture comprising olefin (2) and a polymerization inhibitor.

As further detailed below, the compositions in accordance with the present invention are preferably produced by reacting (1) and (2) in the presence of an effective amount of a polymerization inhibitor.

Due to their desirable properties, the compositions in accordance with the present invention find utility in a wide variety of fields ranging, for example, from lubricants to emulsifiers, coating additives to cosmetics and detergents to plasticizers. As indicated before, however, they have been found especially suitable for use as lubricants and lubricant additives, particularly in low viscosity lubricant applications such as in engine oils, gear oils, greases, compressor oils, turbine oils, metal working fluids, machine oils and hydraulic fluids.

As mentioned above, both the lower molecular weight ene reaction products (alkenyl succinic compounds and corresponding hydrogenated alkyl succinic compounds) as well as the higher molecular weight polymerization and hydrogenated polymerization products are well known as lubricants and lubricant additives. When used in the aforementioned lubricant applications, however, each has its shortcomings.

For example, the alkenyl and alkyl succinic compounds are characterized by high volatility, high color, high acid values, very low viscosity and less than optimal lubrication performance.

While the polymerization products have generally been found to be more suitable for use in this area, they still suffer from the disadvantage of high viscosities, which may be limiting to their ability to be used in the aforementioned low viscosity lubricant applications.

The compositions in accordance with the present invention overcome these disadvantages by providing a balance of desirable properties such as, for example, viscosity, viscosity index, pour point, volatility and lubricity, which would not be expected based upon the properties of the known lower molecular weight alkenyl and alkyl succinic products and higher molecular weight polymerization products.

These and other features and advantages of the present invention will be more readily understood by those skilled in the art from a reading of the following detailed description.

DETAILED DESCRIPTION OF THE PREFERRED EMBODIMENTS

As just mentioned, in accordance with the present invention there is provided a composition suitable for use as a lubricant or lubricant additive, which composition comprises the reaction product of (1) an $\alpha,\beta$-unsaturated dicarboxylic compound and (2) an olefinically unsaturated compound, wherein the $\alpha,\beta$-unsaturated dicarboxylic compound is comprised of at least one ester selected from the group consisting of fumaric esters and maleic esters, wherein the esterifying component comprises a monoalcohol having from 4 to 20 carbon atoms;

the olefinically unsaturated compound comprises a mono olefinically unsaturated compound having from 12 to 24 carbon atoms; and the composition comprises a substantial amount of an intermediate molecular weight reaction product of (1) and (2), which intermediate molecular weight reaction product is neither the lower molecular weight ene reaction product nor the higher molecular weight polymerization product of (1) and (2).

As indicated above, suitable $\alpha,\beta$-unsaturated dicarboxylic compounds are fumaric and maleic esters, which include both the monoesters and diesters of fumaric acid, maleic acid and maleic anhydride. The diesters, however, are preferred due to their better stability under more severe conditions. Especially preferred are the fumaric diesters.

As suitable monoalcohols having from 4 to 20 carbon atoms (esterifying components for the fumaric and maleic esters) may be mentioned linear, branched and/or cyclic monoalcohols such as butanols, ethylhexanols, neopentyl alcohols, isodecyl alcohols, phenols and cyclohexanols. More preferred of these are the monoalcohols having from 4 to 12 carbon atoms, and especially from 4 to 8 carbon atoms. Most preferred are 1-butanol and 2-ethylhexanol. Further, it is advantageous to make use of alcohols alkoxylated with from 1 to 10 ethoxy or propoxy units. The original alcohol moiety may then have from 1 to 20 carbon atoms.

The fumaric and maleic esters, component (1) above, may be produced by the esterification of the appropriate of fumaric acid, maleic acid or maleic anhydride. Such esterification reaction is well known to those skilled in the art and need not be further detailed herein.

As suitable monoolefins having from 12 to 24 carbon atoms, component (2) above, may be mentioned a wide variety of $\alpha$-olefins, internal olefins and vinylidene compounds, as well as other branched, aromatic and heterosubstituted monoolefins and mixtures thereof, a number of which are specifically disclosed in many of the previously incorporated U.S. Pat. No. 3,412,111, U.S. Pat. No. 4,192,930, U.S. Pat. No. 4,396,774 and U.S. Pat. No. 4,761,488. Particularly preferred are $\alpha$-olefins, internal olefins and vinylidene compounds having from 12 to 16 carbon atoms, an advantage to these olefins being that products are obtained which exhibit a lower pour point.

It should be noted that commercially available olefins (which may be obtained from various sources, e.g. Ethyl Corporation, Shell Chemical Co., UOP and Chevron Chemical Co., to name a few) are generally mixtures characterized by a predominant olefin species and a predominant or average carbon number content. Such commercially available mixtures comprising in substantial part $\alpha$-olefins with minor amounts of internal olefins and vinylidene compounds are particularly preferred. Further information regarding mixed olefins may be obtained from *Kirk-Othmer Encyclopedia of Chemical Technology*, (1981), Vol. 16, pages 480–499.

As specific examples of suitable $\alpha$-olefins may be mentioned 1-dodecene, 1-tetradecene, 1-hexadecene and 1-octadecene. Preferred among these are the C12 to C16 $\alpha$-olefins, with the C14 to C16 $\alpha$-olefins being most preferred.

In the preferred reaction scheme, components (1) and (2) are reacted in the presence of an effective amount of a suitable polymerization inhibitor. As examples of such may be mentioned the hydroxy aromatic and amino aromatic compounds as disclosed in previously incorporated U.S. Pat. No. 3,412,111. Of these, hydroquinone, p-tert.butylcatechol and p-hydroxyanisole are preferred, with hydroquinone being most preferred.

By "effective amount" is it meant an amount of polymerization inhibitor sufficient to result in the production of a substantial amount of the intermediate molecular weight reaction product. The amount of inhibitor utilized, therefore, may vary widely, but is preferably in the range of from about 0.01% to about 3% by weight, more preferably from about 0.05% to about 2% by weight, and most preferably from about 0.1% to 1% by weight, based upon the combined weight of components (1) and (2).

It is also preferred that the reaction of components (1) and (2) should take place in the substantial absence of the polymerization initiators. Polymerization initiators are well-known in the art and need not be detailed further.

The reaction between components (1) and (2), in the presence of the polymerization inhibitor, is preferably conducted at temperatures from about 180° C. to about 350° C. and, more preferably, from about 200° C. to about 270° C. The reaction may be carried out at subatmospheric, atmospheric or superatmospheric pressures, but preferably atmospheric. The reaction preferably is carried out in the absence of oxygen, i.e. under an inert (nitrogen) atmosphere. Reaction times may vary widely, generally ranging from about 0.5 to about 15 hours and, more preferably, from about 5 to about 12 hours, with the longer reaction times required for the lower reaction temperatures.

Components (1) and (2) may be reacted in widely varying molar ratios, but generally ranging from about 0.15/1 to about 6.0/1, preferably from about 0.25/1 to about 4.0/1, and more preferably from about 0.5/1 to about 2.0/1. Components (1) and (2) may be reacted in a single dose or may be dosed continuously or periodically throughout the reaction cycle. Stepwise dosage of component (1) to the reaction mixture containing (2) is preferred.

The compositions resulting from the reaction of components (1) and (2), when produced in accordance with the present invention, comprise a substantial amount of an intermediate molecular weight reaction product, which is distinguishable from the known lower molecular weight ene reaction product and higher molecular weight polymerization reaction products of the same components. The compositions produced in accordance with the present invention may also contain amounts of one or more of these known lower and higher molecular weight products.

More specifically, the compositions in accordance with the present invention preferably comprise at least about 30% by weight, more preferably at least about 40% by weight, and still more preferably at least about 50% by weight, of the intermediate molecular weight reaction product, and up to about 70% by weight, more preferably up to about 60% by weight, and still more preferably up to about 50% by weight, of the lower molecular weight reaction product. % by weight is based upon the total weight of the reaction products.

It has been found that the intermediate molecular weight reaction product primarily comprises compositions of 3-5 monomeric units, the intermediate molecular weight reaction product overall having a number average molecular weight (Mn) in the range of about 600 to about 1500. Further, it has been found that, of these compositions having 3-5 monomeric units, a greater proportion of the monomeric units are ester-based monomeric units.

It is believed that the intermediate molecular weight reaction product includes compositions such as:

(a) a lower intermediate molecular weight "tandem ene" reaction product, which comprises 3 monomeric units (1 olefin-based unit and 2 ester-based units), as well as, (b) higher intermediate molecular weight oligomerization and/or "multi-ene" products, which comprise 4-5 monomeric units (generally with a greater proportion of ester-based units than olefin-based units).

Such intermediate molecular weight reaction products are not known from the previously incorporated references, nor can they be produced in a reasonable manner by the reaction schemes disclosed therein.

The compositions in accordance with the present invention may additionally be hydrogenated, for example by heating at 130°-200° C. in the presence of a catalyst, e.g., nickel or palladium. An advantage to hydrogenated compositions according to the invention is the improvement of their thermo-oxidative stability. Hydrogenation of these types of compositions is well-known in the art, and need not be detailed further.

It is clear, as demonstrated below, that the compositions in accordance with the present invention possess properties making them distinguishable from those compositions produced in accordance with the known "ene" selective reactions or the known polymerization selective reactions.

These and other aspects of the present invention will be further exemplified by the following specific examples offered by way of illustration and not limitation thereof.

EXAMPLES

In the following examples, compositions were produced from different α,β-unsaturated dicarboxylic compounds and olefinically unsaturated compounds as set forth below and in Tables I-XII.

PART I: Experimental and comparative evidence directed to the polymerization inhibitor embodiment.

The various compounds were reacted via the following four different reaction schemes:

Invention—ester + olefin in the presence of a polymerization inhibitor and in the presence of oxygen Alternative A—anhydride (or acid) + olefin in the presence of a polymerization inhibitor (Step 1), with subsequent esterification (Step 2)

Alternative B—ester + olefin without a polymerization inhibitor and in the presence of oxygen Alternative C—ester + olefin in the presence of a polymerization initiator and in the presence of oxygen The resulting compositions (1) were tested for:

(2,3) product composition (wt % ene reaction product and other reaction products)—by means of gel permeation chromography (GPC);

(4) number average molecular weight (Mn) of the other reaction products—also by means of GPC;

(5,6) viscosity at 40° C. and 100° C. (cSt)—according to ASTM D445;

(7) viscosity index—calculated according to ASTM D2270-79;

(8) acid value (mg KOH/g product)—according to ASTM D 974;

(9) color—by visual inspection;

(10) iodine value—according to DIN 53241;
(11) pour point (°C.)—according to DIN ISO 3016; and
(12) pour point hydrogenated (°C.)—the products were subsequently hydrogenated with PD/C as catalyst, at 150° C., under normal pressure and for about 3 hours. The hydrogenated products were tested for pour point as above.

Process in Accordance with the Present Invention—Examples 1-8

Into a suitable reaction vessel were added:
3 moles of olefin.
3 moles of fumaric diester,
xylene (1% of total weight) and
hydroquinone (0.3% of total weight).

The mixture was then heated to 230° C. for 10 hours, after which the remaining volatiles were removed up to 240° C. in vacuo.

The product yield for the process in accordance with the present invention was, in each case, between about 70%-75%. Product yield in these examples is based upon the total weight of the raw materials.

Alternative A—Comparative Examples A1-A8

Step 1—reaction of maleic anhydride and olefin in the presence of polymerization inhibitor
Into a suitable reaction vessel were added:
3 moles of olefin.
3 moles of maleic anhydride and
hydroquinone (0.3% of total weight),
which were heated to reflux. As the reaction proceeded, the reflux temperature gradually increased (typically to about 230° C. after three hours) and the reaction was continued to completion (typically about another 4 hours at 230° C). The resulting product, which comprised essentially the alkenyl succinic anhydride, was subsequently purified by vacuum distillation.

The product yield after Step 1 was, in each case, between about 70%-75%.

Step 2—esterification of product from Step 1
2 moles of the product from Step 1, 6 moles of an alcohol, 400 g toluene and p-toluenesulfonic acid (about 0.15% of the total weight) were heated to reflux temperature. The water of reaction was removed by means of a Dean-Stark trap. The reaction was complete when no more water was formed (typically about 7 hours). The remaining volatiles were then removed up to 240° C. in vacuo.

Alternative B—Comparative Examples B1-B8

The reaction was carried out as described above for the process in accordance with the present invention, except that no polymerization inhibitor or xylene was added to the reaction mixture.

The product yield was, in each case, between about 70%-75%.

Alternative C—Comparative Examples C1-C8

Into a suitable reaction vessel were added:
3 moles of olefin and
3 moles of fumaric diester, the mixture being heated to 230° C. At this temperature, 0.03 moles (total) of di-t.butylperoxide were added in 10 portions, one portion every 20 minutes. After the addition of the last portion, the contents were kept at 230° C. for an additional hour, then the remaining volatiles were removed up to 240° C. in vacuo.

The product yield was, in each case, between about 85%-90%.

TABLE I

| | | Olefin = α-C12 Esterifying Component = n-butanol | | | |
|---|---|---|---|---|---|
| (1) | Example | 1 | A1 | B1 | C1 |
| (2) | wt % ene product | 40 | 100 | 5 | 4 |
| (3) | wt % other products | 60 | 0 | 95 | 96 |
| (4) | Mn other products | 1100 | — | 3350 | 1350 |
| (5) | viscosity @ 40° C. | 63.8 | 10.5 | 157 | 119.1 |
| (6) | viscosity @ 100° C. | 9.49 | 2.78 | 18.0 | 14.7 |
| (7) | viscosity index | 130 | 108 | 127 | 126 |
| (8) | acid value | 0.8 | 3.3 | 1.1 | 0.62 |
| (9) | color | yellow | brown | yellow | yellow |
| (10) | iodine value | 24 | 65 | 15 | 14 |
| (11) | pour point (°C.) | <−50 | <−50 | −34 | −44 |
| (12) | pour point (°C.) hydrogenated | −34 | −36 | −22 | −45 |

TABLE II

| | | Olefin = α-C14/16 Esterifying Component = n-butanol | | | |
|---|---|---|---|---|---|
| (1) | Example | 2 | A2 | B2 | C2 |
| (2) | wt % ene product | 44 | 100 | 12 | 7 |
| (3) | wt % other products | 56 | 0 | 88 | 93 |
| (4) | Mn other products | 1100 | — | 1350 | 1300 |
| (5) | viscosity @ 40° C. | 40.2 | 14.0 | 104 | 100.0 |
| (6) | viscosity @ 100° C. | 6.9 | 3.40 | 13.5 | 13.1 |
| (7) | viscosity index | 132 | 118 | 128 | 128 |
| (8) | acid value | 0.7 | 5.3 | 0.9 | 0.78 |
| (9) | color | yellow | brown | yellow | yellow |
| (10) | iodine value | 35 | 59 | 20 | 15 |
| (11) | pour point (°C.) | <−50 | <−51 | −36 | −33 |
| (12) | pour point (°C.) hydrogenated | −33 | −28 | −32 | −28 |

TABLE III

| | | Olefin = α-C16 Esterifying Component = n-butanol | | | |
|---|---|---|---|---|---|
| (1) | Example | 3 | A3 | B3 | C3 |
| (2) | wt % ene product | 40 | 100 | 3 | 5 |
| (3) | wt % other products | 60 | 0 | 97 | 95 |
| (4) | Mn other products | 1200 | — | 1420 | 1400 |
| (5) | viscosity @ 40° C. | 35.2 | 14.8 | 240 | 117.4 |
| (6) | viscosity @ 100° C. | 6.7 | 3.69 | 24.7 | 15.3 |
| (7) | viscosity index | 145 | 142 | 130 | 135 |
| (8) | acid value | 0.8 | 2.4 | — | 0.6 |
| (9) | color | yellow | brown | yellow | yellow |
| (10) | iodine value | 35 | 58 | 13 | 15 |
| (11) | pour point (°C.) | −44 | −31 | — | −12 |
| (12) | pour point (°C.) hydrogenated | −17 | −10 | — | −11 |

TABLE IV

| | | Olefin = α-C20/24 Esterifying Component = n-butanol | | | |
|---|---|---|---|---|---|
| (1) | Example | 4 | A4 | B4 | C4 |
| (2) | wt % ene product | 41 | 95 | 7 | 6 |
| (3) | wt % other products | 59 | 5[1] | 93 | 94 |
| (4) | Mn other products | 1380 | — | 1600 | 1600 |
| (5) | viscosity @ 40° C. | 55.2 | 40.6 | 207 | 150.6 |
| (6) | viscosity @ 100° C. | 9.3 | 6.81 | 20.1 | 18.4 |
| (7) | viscosity index | 151 | 125 | 112 | 137 |
| (8) | acid value | 0.8 | 5.0 | 1.2 | 0.8 |
| (9) | color | brown | brown | brown | brown |
| (10) | iodine value | 27 | 37 | 13 | 14 |
| (11) | pour point (°C.) | +17 | +15 | >+20 | +20 |
| (12) | pour point (°C.) hydrogenated | +20 | +20 | >+20 | >+20 |

[1] = portions not removable during Step 1 purification

TABLE V

Olefin = α-C12
Esterifying Component = 2-ethylhexanol

| (1) | Example | 5 | A5 | B5 | C5 |
|---|---|---|---|---|---|
| (2) | wt % ene product | 35 | 100 | 15 | 4 |
| (3) | wt % other products | 65 | 0 | 85 | 96 |
| (4) | Mn other products | 1400 | — | 1500 | 1350 |
| (5) | viscosity @ 40° C. | 84.4 | 18.8 | 206 | 138.7 |
| (6) | viscosity @ 100° C. | 10.9 | 3.98 | 21.0 | 15.7 |
| (7) | viscosity index | 116 | 108 | 121 | 118 |
| (8) | acid value | 1.3 | 1.5 | 1.4 | 1.0 |
| (9) | color | yellow | brown | yellow | yellow |
| (10) | iodine value | 34 | 51 | 13 | 14 |
| (11) | pour point (°C.) | <−50 | <−50 | −36 | −40 |
| (12) | pour point (°C.) hydrogenated | −45 | −52 | −36 | −42 |

TABLE VI

Olefin = α-C14/16
Esterifying Component = 2-ethylhexanol

| (1) | Example | 6 | A6 | B6 | C6 |
|---|---|---|---|---|---|
| (2) | wt % ene product | 52 | 100 | 21 | 8 |
| (3) | wt % other products | 48 | 0 | 79 | 92 |
| (4) | Mn other products | 1340 | — | 1400 | 1400 |
| (5) | viscosity @ 40° C. | 40.6 | 24.8 | 128 | 122.2 |
| (6) | viscosity @ 100° C. | 6.7 | 4.78 | 14.9 | 14.5 |
| (7) | viscosity index | 118 | 114 | 119 | 120 |
| (8) | acid value | 1.0 | 6.5 | 1.4 | 1.4 |
| (9) | color | yellow | brown | yellow | yellow |
| (10) | iodine value | 30 | 48 | 13 | 14 |
| (11) | pour point (°C.) | <−50 | <−55 | −42 | −38 |
| (12) | pour point (°C.) hydrogenated | <−40 | −53 | −44 | −38 |

TABLE VII

Olefin = α-C16
Esterifying Component = 2-ethylhexanol

| (1) | Example | 7 | A7 | B7 | C7 |
|---|---|---|---|---|---|
| (2) | wt % ene product | 48 | 100 | 10 | 5 |
| (3) | wt % other products | 52 | 0 | 90 | 95 |
| (4) | Mn other products | 1100 | — | 1600 | 1450 |
| (5) | viscosity @ 40° C. | 49.6 | 24.8 | 173 | 138.2 |
| (6) | viscosity @ 100° C. | 7.8 | 5.02 | 18.9 | 16.0 |
| (7) | viscosity index | 124 | 132 | 125 | 122 |
| (8) | acid value | 1.0 | 1.1 | 1.4 | 1.0 |
| (9) | color | yellow | brown | yellow | yellow |
| (10) | iodine value | 29 | 46 | 12 | 14 |
| (11) | pour point (°C.) | <−50 | <−50 | −36 | −18 |
| (12) | pour point (°C.) hydrogenated | −26 | −36 | −34 | −18 |

TABLE VIII

Olefin = α-C20/24
Esterifying Component = 2-ethylhexanol

| (1) | Example | 8 | A8 | B8 | C8 |
|---|---|---|---|---|---|
| (2) | wt % ene product | 50 | 95 | 8 | 8 |
| (3) | wt % other products | 50 | 5¹ | 92 | 92 |
| (4) | Mn other products | 1500 | — | 1900 | 1650 |
| (5) | viscosity @ 40° C. | 82.0 | 55.1 | 266 | 192.3 |
| (6) | viscosity @ 100° C. | 11.2 | 8.86 | 26.7 | 21.4 |
| (7) | viscosity index | 126 | 138 | 131 | 133 |
| (8) | acid value | 2.4 | 8.6 | 2.0 | 1.3 |
| (9) | color | brown | brown | brown | brown |
| (10) | iodine value | 24 | 44 | 11 | 13 |
| (11) | pour point (°C.) | +14 | +04 | +15 | +20 |
| (12) | pour point (°C.) hydrogenated | +20 | +03 | +16 | +16 |

¹ = portions not removable during Step 1 purification

These results show a clear distinction between the compositions in accordance with the present invention as compared to the lower molecular weight alkenyl and alkyl succinic reaction products (Alternate A), and higher molecular weight polymerization products (Alternates B and C) produced in accordance with the alternative processes. That such a divergence in product composition and properties would exist with just a minor variance in the apparent product composition is, in and of itself, clearly unexpected.

Additionally, these results clearly show that the "other" products, which comprise a substantial amount of the compositions in accordance with the present invention, are neither the lower molecular weight alkenyl succinic products nor the higher molecular weight polymerization products, and in fact are intermediate in molecular weight with respect thereto.

COMPARATIVE EXAMPLES D1 AND D2

The following mixtures were made:
D1: mixture of A2 (ene product) and C2 (polymerization product)
D2: mixture of A6 (ene product) and C6 (polymerization product)

Various properties of these mixtures were measured as described above. Table IX below provides a comparison, respectively, of mixture D1 to the reaction product of Example 2, and mixture D2 to the reaction product of Example 6.

TABLE IX

| (1) | Example | 2 | D1 | 6 | D2 |
|---|---|---|---|---|---|
| (2) | wt % ene product | 44 | 44 | 52 | 52 |
| (3) | wt % other products | 56 | 56 | 48 | 48 |
| (4) | Mn other products | 1100 | 1300 | 1340 | 1400 |
| (5) | viscosity @ 40° C. | 40.2 | 67.8 | 40.6 | 70.2 |
| (6) | viscosity @ 100° C. | 6.9 | 10.8 | 6.7 | 10.1 |
| (7) | viscosity index | 132 | 150 | 118 | 128 |
| (11) | pour point (°C.) | <−50 | −42 | <−50 | −34 |

These comparative examples further emphasize the difference in the reaction products in accordance with the present invention over those in accordance with the alternative processes. Particularly noteworthy is the clear demonstration that the "other" reaction products produced in accordance with the present invention are not the same as the polymerization reaction products, as mixtures in equal proportions with the ene product produce compositions with markedly different properties.

PART II Experimental and Comparative Data on the Various Preparation Methods.

In Table X the results have been outlined of experiments establishing the influence of inhibitor presence, oxygen exclusion and ester dosage. The basic procedure was comprised of reacting 3 moles of $C_{16}$ α-olefin and 3 moles of dibutyl fumarate at 250° C. Varied were:

0.3% p-hydroxy anisole (present or not)
oxygen (excluded or not)
ester dosage ("no" means: added in one go and heated for 6 hours, "yes" means: dosed within 4 hours and heated for a further 2 hours).

TABLE X

| Inhibitor Present | Oxygen Present | Ester Dosed | Product Composition 1:1 adduct | others | Viscosity (100° C.) |
|---|---|---|---|---|---|
| | | yes | 53% | 47% | 5.72 cs |
| yes (0.3%) | no | no | 53% | 47% | 5.72 cs |
| | | yes | 36% | 64% | 8.27 cs |
| | yes | no | 30% | 70% | 9.65 cs |
| | | yes | 44% | 56% | 6.75 cs |
| | no | no | 40% | 60% | 7.04 cs |
| no | yes | | 30% | 70% | 9.74 cs |

TABLE X-continued

| Inhibitor Present | Oxygen Present | Ester Dosed | Product Composition | | Viscosity (100 C.) |
|---|---|---|---|---|---|
| | | | 1:1 adduct | others | |
| yes | no | | 10% | 90% | 14.3 cs |

Table X shows that products according to the invention are prepared provided the inhibitor is present, oxygen is excluded or the ester is dosed. The product at the bottom of Table X is not in accordance with the present invention.

PART III Influence of Ester and Olefin Chain Length

Basically following the procedure according to Part I, Examples 1-8 Comparative Examples E1-E4 were prepared. For clarity a comparison is made with Examples 1 and 2.

| | |
|---|---|
| 1: | C12 α-olefin and C4 diester (dibutyl fumarate) |
| 2: | C14/16 α-olefin and C4 diester (dibutyl fumarate) |
| E1: | C10 α-olefin and C4 diester (dibutyl fumarate) |
| E2: | C10 α-olefin and C2 diester (diethyl fumarate) |
| E3: | C14/16 α-olefin and C1 diester (dimethyl fumarate) |
| E4: | C14/16 α-olefin and C1 diester (dimethyl maleate) |

The results have been outlined in Table XI

TABLE XI

| (1) Example | 1 | 2 | E1 | E2 | E3 | E4 |
|---|---|---|---|---|---|---|
| (2) wt % ene product | 40 | 44 | 3% | 15% | 45% | 30% |
| (3) wt % other products | 60 | 56 | 91% | 85% | 55% | 70% |
| (4) Mn other products | 1100 | 1100 | 2200 | 2600, 20000 | 1000 | 1200 |
| (5) viscosity at 40° C. (cSt) | 63.8 | 40.2 | 224 | *) | 103 | 176 |
| (6) viscosity at 100° C.(cSt) | 9.49 | 6.9 | 24.6 | *) | 9.39 | 13.5 |
| (7) viscosity index | 130 | 132 | 138 | *) | 62 | 65 |
| (11) pour point (°C.) | <−50 | <−50 | −39 | *) | −26 | −24 |

*) In a poor yield (25%) a reaction product was obtained which displayed such inhomogeneity that measurements could not be conducted From Table XI it can be learned that the olefin chain length is critical for obtaining the favorably characterized products according to the invention, which is apparent from the unexpectedly large viscosity difference.

From Table XI it can further be learned that ester compounds having a chain shorter than C4 prove unsuitable as a lubricant or lubricant additive on the basis of the low viscosity index. Further it is apparent that the products in accordance with the present invention exhibit much lower pour points than their analogues outside the scope of the invention.

PART IV Various Experimental Data

Examples 9-11 (in Accordance with the Present Invention)

(9) Into a suitable reaction vessel were added: 3 moles of C14/16 α-olefin p-hydroxy anisole (0.3 % of total weight), the mixture being flushed with nitrogen. The mixture was then heated to 250° C. and 3 moles of dibutyl fumarate were added within a period of 4 hours. After a further period of 2 hours the remaining volatiles were removed at 240° C. under vacuo.

(10) The procedure according to Example 9 was followed, but with 6 moles C14/16 α-olefin (and 3 moles of dibutyl fumarate).

(11) The procedure according to Example 9 was followed, but with 3 moles of di(methyl diglycol)fumarate replacing the dibutyl fumarate.

The results of Examples 9-11 have been outlined in Table XII

TABLE XII

| (1) Example | 9 | 10 | 11 |
|---|---|---|---|
| (2) wt % ene product | 52 | 50 | 45 |
| (3) wt % other products | 48 | 50 | 55 |
| (4) Mn other products | 1100 | 1000 | 1400 |
| (5) viscosity @ 40° C. | 32.7 | 28.3 | 41.3 |
| (6) viscosity @ 100° C. | 6.12 | 5.59 | 7.1 |
| (7) viscosity index | 137 | 140 | 135 |
| (10) Iodine value | 35 | 36 | 32 |
| (11) pour point (°C.) | <−40° C. | −39° C. | not determined |

Many modifications and variations besides the embodiments specifically mentioned may be made in the compositions and processes described herein without substantially departing from the concept of the present invention. Accordingly, it should be clearly understood that the form of the invention described herein is exemplary only, and is not intended as a limitation on the scope thereof.

We claim:

1. A composition suitable for use as a lubricant or lubricant additive, which composition comprises the reaction product of (1) an α,β-unsaturated dicarboxylic compound and (2) an olefinically unsaturated compound, wherein the α,β-unsaturated dicarboxylic compound is comprised of at least one ester selected from the group consisting of fumaric esters and maleic esters, wherein the esterifying component comprises a monoalcohol having from 4 to 20 carbon atoms; the olefinically unsaturated compound comprises a monoolefinically unsaturated compound having from 12 to 24 carbon atoms; and the composition comprises at least about 30% by weight of (3) an intermediate molecular weight reaction product of (1) and (2), which intermediate molecular weight reaction product is neither the lower molecular weight ene reaction product nor the higher molecular weight polymerization product of (1) and (2).

2. The composition according to claim 1, wherein the intermediate molecular weight reaction product (3) comprises compositions of 3-5 monomeric units.

3. The composition according to claim 1 wherein the intermediate molecular weight reaction product comprises a number average molecular weight in the range of about 600 to about 1500.

4. The composition according to claim 1, wherein the reaction product of components (1) and (2) comprises: at least about 30% by weight of the intermediate molecular weight reaction product (3), and up to about 70% by weight of the lower molecular weight ene reaction product of components (1) and (2), wherein % by weight is based upon the total weight of the reaction products.

5. The composition according to claim 1, wherein the component (2) is selected from the group consisting of α-olefin compounds, internal olefin compounds vinylidene compounds and mixture thereof.

6. The composition according to claim 5, wherein component (2) is an olefin mixture comprising in substantial part an α-olefin compound, along with an internal olefin compound and a vinylidene compound.

7. The composition according to claim 5, wherein said olefin mixture has an average of 14 to 18 carbon atoms.

8. The composition according to claim 1 wherein component (1) is selected from the group consisting of fumaric diesters and maleic diesters.

9. The composition according to claim 8 wherein component (1) is a fumaric diester.

10. The composition according to claim 1 wherein the esterifying component is a monoalcohol having from 4 to 8 carbon atoms.

11. The composition according to claim 10 wherein the esterifying component comprises a monoalcohol having 4 carbon atoms.

12. The composition according to claim 1 wherein the esterifying component comprises an alkoxylated monoalcohol.

13. The composition according to claim 12 wherein the monoalcohol comprises from 1 to 10 alkoxy units selected from the group consisting of ethoxy and propoxy.

14. The composition according to claim 1 wherein the reaction product has been hydrogenated.

15. A lubricant comprised of the composition of claim 1.

16. A lubricant additive comprised of the composition of claim 1.

17. A process for producing a composition suitable for use as a lubricant or lubricant additive, said process comprised of reacting, in the presence of an effective amount of a polymerization inhibitor, (1) an α,β-unsaturated dicarboxylic compound comprised of at least one ester selected from the group consisting of fumaric esters and maleic esters, wherein the esterifying component comprises a monoalcohol having from 4 to 20 carbon atoms; (2) an olefinically unsaturated compound comprising a monoolefinically unsaturated compound having from 12 to 24 carbon atoms.

18. The process according to claim 17, wherein components (1) and (2) are reacted in the presence of an effective amount of a polymerization inhibitor and in the substantial absence of a polymerization initiator.

19. The process according to claim 17, wherein components (1) and (2) are reacted in the presence of from about 0.01% to about 3% by weight, based upon the combined weight of components (1) and (2), of the polymerization inhibitor.

20. The process according to claim 19, wherein the components (1) and (2) are reacted in the presence of from about 0.05% to about 2% by weight, based upon the combined weight of components (1) and (2), of the polymerization inhibitor.

21. The process according to claim 20, wherein the components (1) and (2) are reacted in the presence of from about 0.1% to about 1% by weight, based upon the combined weight of components (1) and (2), of the polymerization inhibitor.

22. The process according to claim 21, wherein the polymerization inhibitor is selected from the group consisting of hydroxy aromatic compounds or amine aromatic compounds.

23. The process according to claim 22, wherein the polymerization inhibitor is selected from the group consisting of hydroquinone, p-tert.butylcatechol, p-hydroxyanisole and mixtures thereof.

24. The process according to claim 17, wherein components (1) and (2) are reacted in the presence of the at least one polymerization inhibitor at a temperature of from about 180° C. to about 350° C.

25. The process according to claim 24, wherein components (1) and (2) are reacted in the presence of the at least one polymerization inhibitor at a temperature of from about 200° C. to about 270° C.

26. The process according to claim 17, wherein components (1) and (2) are reacted for from about 2 to about 15 hours.

27. The process according to claim 17, wherein components (1) and (2) are reacted in molar ratios of from about 0.15/1 to about 6.0/1.

28. The process according to claims 17, wherein components (1) and (2) are reacted in the absence of oxygen.

29. A process for producing a composition suitable for use as a lubricant or lubricant additive, said process comprised of reacting, without oxygen,
   (1) an α,β-unsaturated dicarboxylic compound comprised of at least one ester selected from the group consisting of fumaric esters and maleic esters, wherein the esterifying component comprises a monoalcohol having from 4 to 20 carbon atoms; and
   (2) an olefinically unsaturated compound comprising a monoolefinically unsaturated compound having from 12 to 24 carbon atoms.

30. A process according to claim 17 wherein the ester component (1) is added to a reaction mixture comprising olefin component (2) by stepwise dosage.

31. A process according to claim 29 wherein the ester component (1) is added to a reaction mixture comprising olefin component (2) by stepwise dosage.

* * * * *